(12) United States Patent
Drexel et al.

(10) Patent No.: US 12,073,361 B2
(45) Date of Patent: *Aug. 27, 2024

(54) AUTOMATED CLINICAL DOCUMENTATION SYSTEM AND METHOD

(71) Applicant: Microsoft Technology Licensing, LLC, Redmond, WA (US)

(72) Inventors: Christina Drexel, Vienna (AT); Ljubomir Milanovic, Vienna (AT)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/955,693

(22) Filed: Sep. 29, 2022

(65) Prior Publication Data
US 2023/0014971 A1 Jan. 19, 2023

Related U.S. Application Data

(63) Continuation of application No. 16/270,888, filed on Feb. 8, 2019, now Pat. No. 11,494,735.
(Continued)

(51) Int. Cl.
*G16H 15/00* (2018.01)
*G06F 3/16* (2006.01)
(Continued)

(52) U.S. Cl.
CPC ............ *G06Q 10/10* (2013.01); *G06F 3/165* (2013.01); *G06F 40/117* (2020.01); *G06F 40/30* (2020.01);
(Continued)

(58) Field of Classification Search
CPC ........ G06Q 10/10; G06Q 50/22; G06F 3/165; G06F 40/117; G06F 40/30; G06F 40/151;
(Continued)

(56) References Cited

U.S. PATENT DOCUMENTS 5,357,427 A  10/1994  Langen et al.
8,132,104 B2  3/2012  Ash et al.
(Continued)

FOREIGN PATENT DOCUMENTS

WO  9844484 A1  10/1998
WO  2005093716 A1  10/2005
(Continued)

OTHER PUBLICATIONS

Jeffrey G Klann and Peter Szolovits, "An intelligent listening framework for capturing encounter notes from a doctor-patient dialog," BMC Medical Informatics and Decision Making 2009, 9(Suppl 1):S3 (Year: 2009).*
(Continued)

*Primary Examiner* — Joshua B Blanchette
(74) *Attorney, Agent, or Firm* — Brian J. Colandreo; Heath M. Sargeant; Holland & Knight LLP

(57) ABSTRACT

A method, computer program product, and computing system for obtaining encounter information of a patient encounter; processing the encounter information to generate an encounter transcript; and processing the encounter transcript to locate one or more procedural events within the encounter transcript.

20 Claims, 9 Drawing Sheets

Related U.S. Application Data

(60) Provisional application No. 62/638,809, filed on Mar. 5, 2018.

(51) Int. Cl.

| | | |
|---|---|---|
| *G06F 40/117* | (2020.01) | |
| *G06F 40/30* | (2020.01) | |
| *G06Q 10/10* | (2023.01) | |
| *G06T 7/20* | (2017.01) | |
| *G10L 15/22* | (2006.01) | |
| *G10L 15/26* | (2006.01) | |
| *G10L 15/30* | (2013.01) | |
| *G10L 25/45* | (2013.01) | |
| *G10L 25/51* | (2013.01) | |
| *G16H 10/20* | (2018.01) | |
| *G16H 10/40* | (2018.01) | |
| *G16H 10/60* | (2018.01) | |
| *G16H 50/70* | (2018.01) | |
| *H04R 1/40* | (2006.01) | |
| *H04R 3/00* | (2006.01) | |

(52) U.S. Cl.
CPC .............. *G06T 7/20* (2013.01); *G10L 15/22* (2013.01); *G10L 15/26* (2013.01); *G10L 15/30* (2013.01); *G10L 25/45* (2013.01); *G10L 25/51* (2013.01); *G16H 10/20* (2018.01); *G16H 10/40* (2018.01); *G16H 10/60* (2018.01); *G16H 15/00* (2018.01); *G16H 50/70* (2018.01); *H04R 1/406* (2013.01); *H04R 3/005* (2013.01); *G06T 2207/30196* (2013.01)

(58) Field of Classification Search
CPC .............. G06F 40/279; G06T 7/20; G06T 2207/30196; G10L 15/22; G10L 15/26; G10L 15/30; G10L 25/45; G10L 25/51; G16H 10/20; G16H 10/40; G16H 10/60; G16H 15/00; G16H 50/70; G16H 30/40; G16H 80/00; H04R 1/406; H04R 3/005
See application file for complete search history.

(56) References Cited

U.S. PATENT DOCUMENTS

| | | |
|---|---|---|
| 8,589,379 B2 | 11/2013 | Hirasawa |
| 9,104,985 B2 | 8/2015 | Drucker et al. |
| 9,479,931 B2 | 10/2016 | Ortiz et al. |
| 9,509,676 B1 | 11/2016 | Johnson et al. |
| 9,658,024 B1 | 5/2017 | Trpkovski |
| 9,679,107 B2 | 6/2017 | Cardoza et al. |
| 10,212,588 B2 | 2/2019 | Grim et al. |
| 10,354,054 B2 | 7/2019 | Kobres et al. |
| 10,546,655 B2 | 1/2020 | Owen et al. |
| 10,650,824 B1 | 5/2020 | Kesharaju et al. |
| 10,691,783 B2 | 6/2020 | Frempong et al. |
| 10,701,081 B2 | 6/2020 | Grim et al. |
| 10,803,436 B2 | 10/2020 | Kobres et al. |
| 10,957,427 B2 | 3/2021 | Owen et al. |
| 10,957,428 B2 | 3/2021 | Owen et al. |
| 10,978,187 B2 | 4/2021 | Owen et al. |
| 11,043,288 B2 | 6/2021 | Gallopyn et al. |
| 11,074,996 B2 | 7/2021 | Gallopyn et al. |
| 11,101,022 B2 | 8/2021 | Owen |
| 11,101,023 B2 | 8/2021 | Gallopyn et al. |
| 11,114,186 B2 | 9/2021 | Owen |
| 11,177,034 B2 | 11/2021 | Lyman et al. |
| 11,295,838 B2 | 4/2022 | Owen et al. |
| 11,295,839 B2 | 4/2022 | Owen et al. |
| 11,316,865 B2 | 4/2022 | Gallopyn et al. |
| 11,322,231 B2 | 5/2022 | Owen et al. |
| 11,368,454 B2 | 6/2022 | Whaley et al. |
| 11,402,976 B1 | 8/2022 | Palamadai et al. |
| 11,483,707 B2 | 10/2022 | Leblang et al. |
| 11,538,567 B2 | 12/2022 | Davies |
| 2001/0044588 A1 | 11/2001 | Mault |
| 2003/0051214 A1 | 3/2003 | Graham et al. |
| 2003/0105631 A1 | 6/2003 | Habte |
| 2005/0154588 A1 | 7/2005 | Janas et al. |
| 2006/0069545 A1 | 3/2006 | Wu et al. |
| 2006/0106645 A1 | 5/2006 | Bergelson et al. |
| 2008/0222734 A1 | 9/2008 | Redlich et al. |
| 2008/0243544 A1 | 10/2008 | Cafer |
| 2009/0023555 A1 | 1/2009 | Raymond |
| 2009/0089082 A1 | 4/2009 | Heckerman et al. |
| 2009/0132276 A1 | 5/2009 | Petera |
| 2009/0157385 A1 | 6/2009 | Tian et al. |
| 2009/0248444 A1 | 10/2009 | Harnick |
| 2009/0304254 A1 | 12/2009 | Yoshida |
| 2010/0094650 A1* | 4/2010 | Tran .................. G16H 40/20 705/2 |
| 2010/0191519 A1 | 7/2010 | Morton et al. |
| 2011/0254954 A1 | 10/2011 | Lee |
| 2012/0041949 A1 | 2/2012 | Hirasawa et al. |
| 2012/0173269 A1 | 7/2012 | Omidi |
| 2012/0173278 A1 | 7/2012 | Herbst et al. |
| 2012/0197648 A1 | 8/2012 | Moloney |
| 2012/0209625 A1 | 8/2012 | Armstrong et al. |
| 2012/0323589 A1* | 12/2012 | Udani .................. G06Q 50/18 707/769 |
| 2012/0330876 A1 | 12/2012 | Bryce |
| 2013/0246329 A1 | 9/2013 | Pasquero et al. |
| 2013/0317838 A1 | 11/2013 | Schoenberg |
| 2014/0013219 A1 | 1/2014 | Liu |
| 2014/0047375 A1 | 2/2014 | Koll et al. |
| 2014/0164994 A1 | 6/2014 | Myslinski |
| 2014/0188516 A1 | 7/2014 | Kamen et al. |
| 2014/0253876 A1 | 9/2014 | Klin |
| 2014/0275928 A1 | 9/2014 | Acquista et al. |
| 2014/0278448 A1 | 9/2014 | Sadeghi et al. |
| 2014/0282008 A1 | 9/2014 | Verard |
| 2015/0106123 A1 | 4/2015 | Amarasingham |
| 2015/0149207 A1 | 5/2015 | O'keefe |
| 2015/0154358 A1 | 6/2015 | Anderson et al. |
| 2015/0220637 A1 | 8/2015 | Goetz |
| 2016/0063191 A1 | 3/2016 | Vesto et al. |
| 2016/0110350 A1 | 4/2016 | Waibel |
| 2016/0210429 A1 | 7/2016 | Ortiz et al. |
| 2016/0239617 A1 | 8/2016 | Farooq et al. |
| 2016/0364526 A1 | 12/2016 | Reicher et al. |
| 2016/0366299 A1 | 12/2016 | Sato |
| 2017/0006135 A1 | 1/2017 | Siebel et al. |
| 2017/0039502 A1 | 2/2017 | Guman |
| 2017/0083214 A1 | 3/2017 | FuresjÖet al. |
| 2017/0098051 A1 | 4/2017 | Balram |
| 2017/0116392 A1* | 4/2017 | Casella dos Santos ............ G16H 10/60 |
| 2017/0185716 A1 | 6/2017 | Rodriguez et al. |
| 2017/0277993 A1 | 9/2017 | Beaver |
| 2017/0295075 A1 | 10/2017 | Roebuck |
| 2017/0300648 A1 | 10/2017 | Charlap |
| 2019/0034604 A1 | 1/2019 | Zheng et al. |
| 2019/0051374 A1 | 2/2019 | Vozila et al. |
| 2019/0051375 A1 | 2/2019 | Owen et al. |
| 2019/0051376 A1 | 2/2019 | Gallopyn et al. |
| 2019/0051379 A1 | 2/2019 | Owen et al. |
| 2019/0051380 A1 | 2/2019 | Owen et al. |
| 2019/0051394 A1 | 2/2019 | Owen et al. |
| 2019/0066823 A1 | 2/2019 | Owen |
| 2019/0121532 A1 | 4/2019 | Strader et al. |
| 2019/0272145 A1 | 9/2019 | Sharma et al. |
| 2019/0272147 A1 | 9/2019 | Vozila et al. |
| 2019/0272827 A1 | 9/2019 | Vozila |
| 2019/0272895 A1 | 9/2019 | Vozila et al. |
| 2019/0272896 A1 | 9/2019 | Vozila et al. |
| 2019/0272897 A1 | 9/2019 | Öz et al. |
| 2019/0272900 A1 | 9/2019 | Jancsary et al. |
| 2019/0272901 A1 | 9/2019 | Almendro Barreda et al. |
| 2019/0272902 A1 | 9/2019 | Vozila et al. |
| 2019/0272905 A1 | 9/2019 | Almendro Barreda et al. |
| 2019/0272906 A1 | 9/2019 | Vozila et al. |
| 2020/0160951 A1 | 5/2020 | Owen et al. |

(56) References Cited

U.S. PATENT DOCUMENTS

| | | |
|---|---|---|
| 2020/0265842 A1 | 8/2020 | Singh |
| 2020/0372140 A1 | 11/2020 | Jaber et al. |
| 2021/0098098 A1 | 4/2021 | Pinto |
| 2021/0119802 A1 | 4/2021 | Shetty |
| 2021/0210180 A1 | 7/2021 | Owen et al. |
| 2021/0210181 A1 | 7/2021 | Owen et al. |
| 2021/0233634 A1 | 7/2021 | Owen et al. |
| 2021/0233652 A1 | 7/2021 | Owen et al. |
| 2021/0243412 A1 | 8/2021 | Owen et al. |
| 2021/0407635 A1 | 12/2021 | Owen |
| 2022/0051772 A1 | 2/2022 | Gallopyn et al. |
| 2022/0130502 A1 | 4/2022 | Vozila et al. |
| 2022/0138299 A1 | 5/2022 | Gallopyn et al. |
| 2022/0180318 A1 | 6/2022 | Barreda et al. |
| 2022/0208322 A1 | 6/2022 | Owen et al. |
| 2022/0210161 A1 | 6/2022 | Gallopyn et al. |
| 2022/0319653 A1 | 10/2022 | Owen et al. |
| 2023/0021529 A1 | 1/2023 | Bhattacherjee et al. |
| 2023/0092558 A1 | 3/2023 | Vozila et al. |
| 2023/0290023 A1 | 9/2023 | Tsunomori et al. |

FOREIGN PATENT DOCUMENTS

| | | |
|---|---|---|
| WO | 2013118510 A1 | 8/2013 |
| WO | 2015021208 A1 | 2/2015 |
| WO | 2016149794 A1 | 9/2016 |

OTHER PUBLICATIONS

"Final Office Action Issued in U.S. Appl. No. 16/058,803", Mailed Date: Mar. 20, 2023, 12 Pages.
"Notice of Allowance Issued in U.S. Appl. No. 17/210,052", Mailed Date: Jan. 30, 2023, 5 Pages.
"Office Action Issued in European Patent Application No. 18843329.6", Mailed Date: Feb. 24, 2023, 5 Pages.
Shivappa, et al., "Person Tracking With Audio-visual Cues Using The Iterative Decoding Framework", In Proceedings of the IEEE Fifth International Conference on Advanced Video and Signal Based Surveillance, Sep. 1, 2008, pp. 260-267.
Watanabe, et al., "Hybrid CTC/Attention Architecture for End-to-End Speech Recognition", In Journal of IEEE Selected Topics in Signal Processing, vol. 11, Issue 8, Dec. 2017, pp. 1240-1253.
"Non Final Office Action Issued in U.S. Appl. No. 17/991,234", Mailed Date: Mar. 14, 2023, 42 Pages.
"Notice of Allowance Issued in U.S. Appl. No. 17/210,052", Mailed Date: Apr. 10, 2023, 5 Pages.
"Final Office Action Issued in U.S. Appl. No. 17/571,799", Mailed Date: Apr. 25, 2023, 31 Pages.
"Notice of Allowance Issued in U.S. Appl. No. 17/696,165", Mailed Date: Apr. 26, 2023, 7 Pages.
"Notice of Allowance Issued in European Patent Application No. 18843586.1", Mailed Date: Mar. 14, 2023, 8 Pages.
"Notice of Allowance Issued In European Patent Application No. 18843586.1", Mailed Date: Jun. 9, 2023, 2 Pages.
"Final Office Action Issued in U.S. Appl. No. 17/991,234", Mailed Date: Jul. 11, 2023, 35 Pages.
"Non Final Office Action Issued in U.S. Appl. No. 17/571,799", Mailed Date: Jul. 27, 2023, 29 Pages.
Non-Final Office Action mailed on Dec. 11, 2023, in U.S. Appl. No. 17/697,593, 23 Pages.
"Preventing Healthcare Fraud with Voice Biometrics", Retrieved From: https://www.interactions.com/blog/compliance-and-security/voice-biometrics-for-healthcare/, Apr. 5, 2017, 4 Pages.
"Notice of Allowance Issued in U.S. Appl. No. 16/038,886", Mailed Date: Nov. 4, 2021, 12 Pages.
"Non Final Office Action Issued in U.S. Appl. No. 16/058,803", Mailed Date: Sep. 21, 2022, 11 Pages.
"Notice of Allowance Issued in U.S. Appl. No. 16/058,829", Mailed Date : Jun. 3, 2022, 9 Pages.
"Notice of Allowance Issued in U.S. Appl. No. 16/058,883", Mailed Date: Jun. 2, 2022, 2 Pages.
"Notice of Allowance Issued in U.S. Appl. No. 16/058,914", Mailed Date: Sep. 14, 2022, 11 Pages.
"Final Office Action Issued in U.S. Appl. No. 16/058,925", Mailed Date: Oct. 20, 2022, 23 Pages.
"Advisory Action Issued in U.S. Appl. No. 16/058,936", Mailed Date: Aug. 19, 2020, 5 Pages.
"Final Office Action issued in related U.S. Appl. No. 16/058,936", Mailed Date: Dec. 22, 2020, 28 Pages.
"Notice of Allowance Issued in U.S. Appl. No. 16/058,951", Mailed Date: Nov. 15, 2019, 11 Pages.
"Final Office Action Issued in U.S. Appl. No. 16/059,818", Mailed Date: Apr. 7, 2020, 7 Pages.
"Advisory Action Issued In U.S. Appl. No. 16/059,895", Mailed Date: Sep. 10, 2020, 5 Pages.
"Advisory Action Issued In U.S. Appl. No. 16/059,974", Mailed Date: Sep. 15, 2020, 5 Pages.
"Advisory Action Issued In U.S. Appl. No. 16/059,986", Mailed Date: Sep. 15, 2020, 5 Pages.
"Final Office Action issued in related U.S. Appl. No. 16/100,030", Mailed Date: May 8, 2020, 10 Pages.
"Notice of Allowance Issued in U.S. Appl. No. 16/192,358", Mailed Date: Dec. 8, 2021, 8 Pages.
"Notice of Allowance issued in related U.S. Appl. No. 16/271,616", Mailed Date: Mar. 17, 2020, 11 Pages.
"Final Office Action Issued in U.S. Appl. No. 16/292,877", Mailed Date: Nov. 14, 2022, 10 Pages.
"Final Office Action Issued in U.S. Appl. No. 16/292,895", Mailed Date: Nov. 30, 2020, 14 Pages.
"Final Office Action Issued in U.S. Appl. No. 16/292,973", Mailed Date: Oct. 28, 2022, 27 Pages.
"Final Office Action Issued in U.S. Appl. No. 16/588,475", Mailed Date: Apr. 28, 2022, 18 Pages.
"Non Final Office Action Issued in U.S. Appl. No. 16/588,475", Mailed Date: Sep. 16, 2022, 17 Pages.
"Notice of Allowance Issued in U.S. Appl. No. 17/084,310", Mailed Date: Aug. 13, 2021, 12 Pages.
"Notice of Allowance Issued in U.S. Appl. No. 17/210,052", Mailed Date: Sep. 9, 2022, 8 Pages.
"Non Final Office Action Issued in U.S. Appl. No. 17/210,120", Mailed Date: Nov. 1, 2021, 14 Pages.
"Notice of Allowance Issued in U.S. Appl. No. 17/210,120", Mailed Date: Jun. 10, 2022, 7 Pages.
"Notice of Allowance Issued in U.S. Appl. No. 17/467,688", Mailed Date: Oct. 6, 2022, 9 Pages.
"Non Final Office Action Issued in U.S. Appl. No. 17/571,799", Mailed Date: Dec. 6, 2022, 26 Pages.
"Non Final Office Action Issued in U.S. Appl. No. 17/571,819", Mailed Date: Nov. 7, 2022, 14 Pages.
"Non Final Office Action Issued in U.S. Appl. No. 17/696,165", Mailed Date: Nov. 25, 2022, 7 Pages.
"Office Action Issued in European Patent Application No. 18844675.1", Mailed Date: Mar. 4, 2022, 6 Pages.
"Extended European Search Report Issued in European Application No. 18844829.4", Mailed Date: Apr. 30, 2021, 9 Pages.
"Extended European Search Report Issued in Application No. 19763338.1", Mailed Date: Apr. 4, 2022, 8 Pages.
"European Extended Search Report for Application No. 19763474.4", Mailed Date: Apr. 8, 2022, 8 Pages.
"Extended European Search Report Issued in Application No. 19763475.1", Mailed Date: Apr. 12, 2022, 10 Pages.
"Search Report Issued in European Patent Application No. 19763477.7", Mailed Date: Mar. 28, 2022, 10 Pages.
"Search Report Issued in European Patent Application No. 19763600.4", Mailed Date: Mar. 31, 2022, 9 Pages.
"Search Report Issued in European Patent Application No. 19763678.0", Mailed Date: Mar. 25, 2022, 8 Pages.
"Search Report Issued in European Patent Application No. 19763834.9", Mailed Date: Dec. 10, 2021, 9 Pages.
"Search Report Issued in European Patent Application No. 19764329.9", Mailed Date: Dec. 14, 2021, 13 Pages.

(56) References Cited

OTHER PUBLICATIONS

"International Search Report and Written Opinion Issued in PCT Application No. PCT/US21/056274", Mailed Date: Dec. 7, 2021, 7 Pages.
"Invitation To Pay Additional Fees Issued in PCT Application No. PCT/US22/021393", Mailed Date: Jun. 24, 2022, 2 Pages.
"Invitation To Pay Additional Fees Issued in PCT Application No. PCT/US22/021412", Mailed Date: Jun. 24, 2022, 2 Pages.
"International Search Report and Written Opinion Issued in PCT Application No. PCT/US22/021419", Mailed Date: Sep. 23, 2022, 13 Pages.
"Invitation To Pay Additional Fees Issued in PCT Application No. PCT/US22/021419", Mailed Date: Jul. 5, 2022, 2 Pages.
"Invitation To Pay Additional Fees Issued in PCT Application No. PCT/US22/021422", Mailed Date: Jun. 24, 2022, 2 Pages.
Pusateri, et al., "A Mostly Data-Driven Approach to Inverse Text Normalization", In Proceedings of Interspeech, Aug. 20, 2017, pp. 2784-2788.
Shen, et al., "Auto-encoding twin-bottleneck hashing", In Proceedings of the IEEE/CVF Conference on Computer Vision and Pattern Recognition, Jun. 13, 2020, pp. 2818-2827.
"Notice of Allowance Issued in U.S. Appl. No. 16/058,914", Mailed Date: Jan. 5, 2023, 11 Pages.
"Final Office Action Issued in U.S. Appl. No. 16/292,895", Mailed Date: Jan. 5, 2023, 17 Pages.
"Non Final Office Action Issued in U.S. Appl. No. 17/210,233", Mailed Date: Oct. 23, 2023, 47 Pages.
"Non Final Office Action Issued in U.S. Appl. No. 17/846,355", Mailed Date: Sep. 27, 2023, 16 Pages.
"Non Final Office Action Issued in U.S. Appl. No. 17/678,791", Mailed Date: Nov. 9, 2023, 8 Pages.
Sapru, et al., "Improving Speaker Diarization using Social Role Information", In Proceedings of International Conference on Acoustics, Speech and Signal Processing, May 4, 2014, pp. 101-105.
Notice of Allowance mailed on Feb. 14, 2024, in U.S. Appl. No. 17/571,799, 7 pages.
Notice of Allowance mailed on Jan. 31, 2024 in U.S. Appl. No. 17/846,355, 8 Pages.
Communication pursuant to Article 94(3) EPC Received for European Application No. 18843254.6, mailed on Mar. 26, 2024, 08 pages.
Communication Pursuant to Article 94(3) EPC, Received for European Application No. 18844407.9, mailed on Feb. 14, 2024, 06 pages.
Communication pursuant to Article 94(3) Received in European Patent Application No. 18844226.3, mailed on Mar. 22, 2024, 7 pages.
Final Office Action mailed on Mar. 7, 2024, in U.S. Appl. No. 17/210,233, 54 pages.
Communication 94(3) Received for European Application No. 18844406.1, mailed on Apr. 4, 2024, 11 pages.
Communication 94(3) Received for European Application No. 18844669.4, mailed on Apr. 3, 2024, 5 pages.
Communication 94(3) Received for European Application No. 18844829.4, mailed on Apr. 4, 2024, 5 pages.
Communication pursuant to Article 94(3) EPC Received for European Application No. 18843255.3, mailed on Feb. 26, 2024, 6 pages.
Communication pursuant to Article 94(3) EPC, Received for European Application No. 18843175.3, mailed on Feb. 29, 2024, 09 pages.
Communication pursuant to Article 94(3) EPC, Received for European Application No. 18843945.9, mailed on Mar. 4, 2024, 09 pages.
Communication pursuant to Article 94(3) received in European Application No. 18844530.8, mailed on Apr. 3, 2024, 5 pages.
Communication under Rule 71(3) EPC Received for European Application No. 18845046.4, mailed on Feb. 29, 2024, 5 pages.
Non-Final Office Action mailed on Apr. 16, 2024, in U.S. Appl. No. 17/210,300, 13 pages.
Weibel, et al., "Lab-In-A-Box: semi-automatic tracking of activity in the medical office," Personal Ubiquitous Computing, Springer, Sep. 28, 2014, pp. 317-334.
Communication pursuant to Article 94(3) EPC, Received for European Application No. 18843648.9, mailed on May 2, 2024, 10 pages.
Communication pursuant to Article 94(3) received in European Application No. 18843873.3, mailed on Apr. 11, 2024, 5 pages.
Communication pursuant to Article 94(3) Received in European Patent Application No. 18845144.7, mailed on May 3, 2024, 10 pages.
Communication under Rule 71(3) EPC Received for European Application No. 18843874.1, mailed on May 10, 2024, 09 pages.
Non-Final office action mailed on Jun. 21, 2024, in U.S. Appl. No. 17/697,593, 28 pages.
Lee, et al., "Portable meeting recorder.", Proceedings of the tenth ACM international conference on Multimedia, 2002, 10 Pages.

\* cited by examiner

AUTOMATED CLINICAL DOCUMENTATION SYSTEM AND METHOD

RELATED APPLICATION(S)

This application is a continuation of U.S. patent application Ser. No. 16/270,888, filed on Feb. 8, 2029 which claims the benefit of U.S. Provisional Application No. 62/638,809, filed on 5 Mar. 2018; the entire contents of each are incorporated herein by reference.

TECHNICAL FIELD

This disclosure relates to documentation systems and methods and, more particularly, to automated clinical documentation systems and methods.

BACKGROUND

As is known in the art, clinical documentation is the creation of medical records and documentation that details the medical history of medical patients. As would be expected, traditional clinical documentation includes various types of data, examples of which may include but are not limited to paper-based documents and transcripts, as well as various images and diagrams.

As the world moved from paper-based content to digital content, clinical documentation also moved in that direction, where medical records and documentation were gradually transitioned from stacks of paper geographically-dispersed across multiple locations/institutions to consolidated and readily accessible digital content.

SUMMARY OF DISCLOSURE

Tracking Procedural Events

In one implementation, a computer-implemented method is executed on a computing device and includes: obtaining encounter information of a patient encounter; processing the encounter information to generate an encounter transcript; and processing the encounter transcript to locate one or more procedural events within the encounter transcript.

One or more of the following features may be included. Obtaining encounter information of a patient encounter may include one or more of: obtaining encounter information from the medical professional; obtaining encounter information from a patient; and obtaining encounter information obtaining encounter information from a third party. At least a portion of the encounter transcript may be processed to populate at least a portion of a medical record associated with the patient encounter. Processing the encounter transcript to locate one or more procedural events within the encounter transcript may include one or more of: manually-initiating the processing of the encounter transcript to locate one or more procedural events within the encounter transcript; and automatically-initiating the processing of the encounter transcript to locate one or more procedural events within the encounter transcript. Processing the encounter transcript to locate one or more procedural events within the encounter transcript may include associating the one or more procedural events with one or more portions of the encounter information of the patient encounter. The identity of one or more encounter participants of the patient encounter may be confirmed. The one or more procedural events may include one or more of: an informed consent event; a personal medical history event; a family medical history event; a drug allergy event; a drug side-effect event; and a drug warning event.

In another implementation, a computer program product resides on a computer readable medium and has a plurality of instructions stored on it. When executed by a processor, the instructions cause the processor to perform operations including obtaining encounter information of a patient encounter; processing the encounter information to generate an encounter transcript; and processing the encounter transcript to locate one or more procedural events within the encounter transcript.

One or more of the following features may be included. Obtaining encounter information of a patient encounter may include one or more of: obtaining encounter information from the medical professional; obtaining encounter information from a patient; and obtaining encounter information obtaining encounter information from a third party. At least a portion of the encounter transcript may be processed to populate at least a portion of a medical record associated with the patient encounter. Processing the encounter transcript to locate one or more procedural events within the encounter transcript may include one or more of: manually-initiating the processing of the encounter transcript to locate one or more procedural events within the encounter transcript; and automatically-initiating the processing of the encounter transcript to locate one or more procedural events within the encounter transcript. Processing the encounter transcript to locate one or more procedural events within the encounter transcript may include associating the one or more procedural events with one or more portions of the encounter information of the patient encounter. The identity of one or more encounter participants of the patient encounter may be confirmed. The one or more procedural events may include one or more of: an informed consent event; a personal medical history event; a family medical history event; a drug allergy event; a drug side-effect event; and a drug warning event.

In another implementation, a computing system includes a processor and memory is configured to perform operations including obtaining encounter information of a patient encounter; processing the encounter information to generate an encounter transcript; and processing the encounter transcript to locate one or more procedural events within the encounter transcript.

One or more of the following features may be included. Obtaining encounter information of a patient encounter may include one or more of: obtaining encounter information from the medical professional; obtaining encounter information from a patient; and obtaining encounter information obtaining encounter information from a third party. At least a portion of the encounter transcript may be processed to populate at least a portion of a medical record associated with the patient encounter. Processing the encounter transcript to locate one or more procedural events within the encounter transcript may include one or more of: manually-initiating the processing of the encounter transcript to locate one or more procedural events within the encounter transcript; and automatically-initiating the processing of the encounter transcript to locate one or more procedural events within the encounter transcript. Processing the encounter transcript to locate one or more procedural events within the encounter transcript may include associating the one or more procedural events with one or more portions of the encounter information of the patient encounter. The identity of one or more encounter participants of the patient encounter may be confirmed. The one or more procedural events may include one or more of: an informed consent event; a personal medical history event; a family medical history event; a drug allergy event; a drug side-effect event; and a drug warning event.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
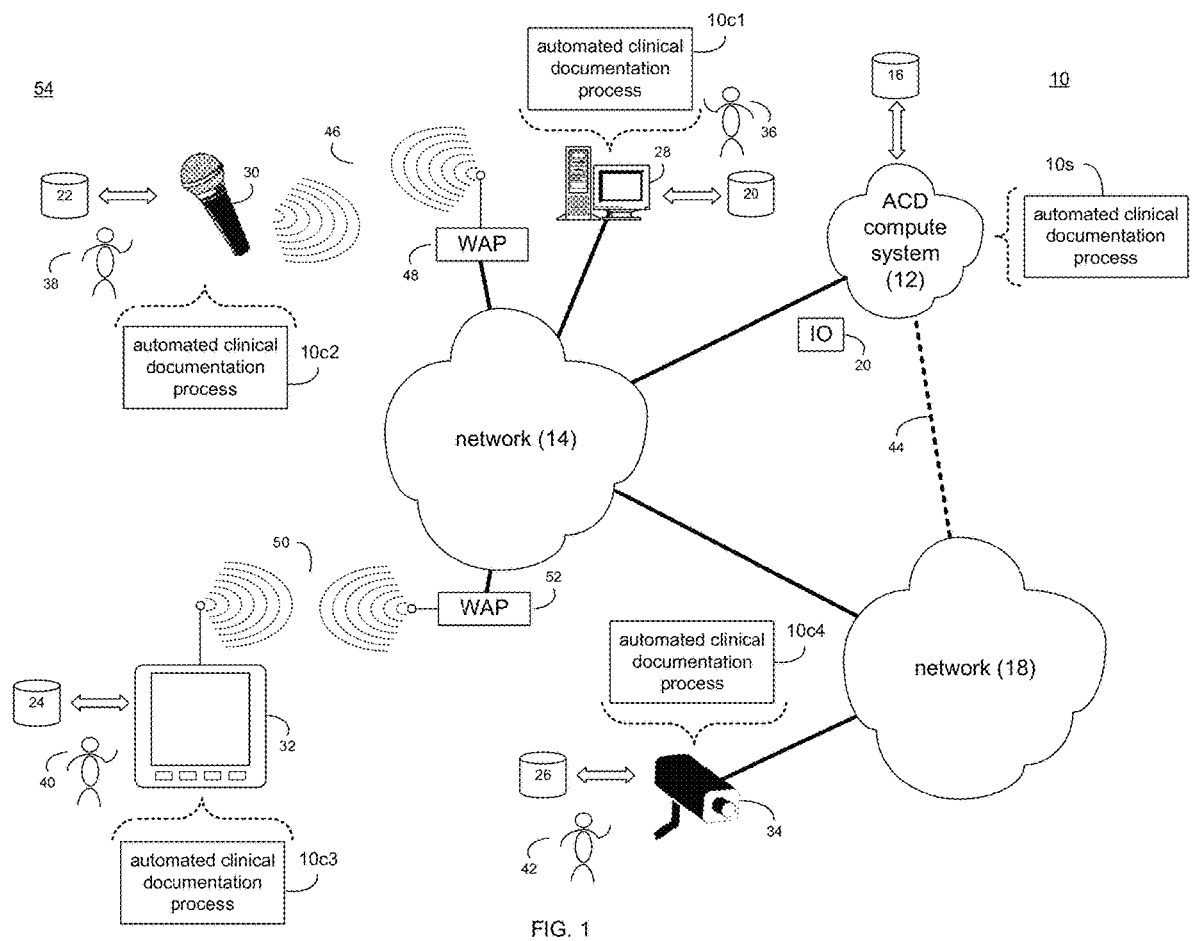
FIG. 1 is a diagrammatic view of an automated clinical documentation compute system and an automated clinical documentation process coupled to a distributed computing network.

Referring to FIG. 1, there is shown automated clinical documentation process 10. As will be discussed below in greater detail, automated clinical documentation process 10 may be configured to automate the collection and processing of clinical encounter information to generate/store/distribute medical records.

Automated clinical documentation process 10 may be implemented as a server-side process, a client-side process, or a hybrid server-side/client-side process. For example, automated clinical documentation process 10 may be implemented as a purely server-side process via automated clinical documentation process 10s. Alternatively, automated clinical documentation process 10 may be implemented as a purely client-side process via one or more of automated clinical documentation process 10c1, automated clinical documentation process 10c2, automated clinical documentation process 10c3, and automated clinical documentation process 10c4. Alternatively still, automated clinical documentation process 10 may be implemented as a hybrid server-side/client-side process via automated clinical documentation process 10s in combination with one or more of automated clinical documentation process 10c1, automated clinical documentation process 10c2, automated clinical documentation process 10c3, and automated clinical documentation process 10c4.

Accordingly, automated clinical documentation process 10 as used in this disclosure may include any combination of automated clinical documentation process 10s, automated clinical documentation process 10c1, automated clinical documentation process 10c2, automated clinical documentation process 10c3, and automated clinical documentation process 10c4.

Automated clinical documentation process 10s may be a server application and may reside on and may be executed by automated clinical documentation (ACD) compute system 12, which may be connected to network 14 (e.g., the Internet or a local area network). ACD compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD compute system 12 may execute one or more operating systems, examples of which may include but are not limited to: Microsoft Windows Server™; Redhat Linux™, Unix, or a custom operating system, for example.

The instruction sets and subroutines of automated clinical documentation process 10s, which may be stored on storage device 16 coupled to ACD compute system 12, may be executed by one or more processors (not shown) and one or more memory architectures (not shown) included within ACD compute system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from automated clinical documentation process 10s, automated clinical documentation process 10c1, automated clinical documentation process 10c2, automated clinical documentation process 10c3 and/or automated clinical documentation process 10c4 to ACD compute system 12. Examples of IO request 20 may include but are not limited to data write requests (i.e. a request that content be written to ACD compute system 12) and data read requests (i.e. a request that content be read from ACD compute system 12).

The instruction sets and subroutines of automated clinical documentation process 10c1, automated clinical documentation process 10c2, automated clinical documentation process 10c3 and/or automated clinical documentation process 10c4, which may be stored on storage devices 20, 22, 24, 26 (respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD compute system 12 directly through network 14 or through secondary network 18. Further, ACD compute system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™, or a custom operating system, wherein the combination of the various ACD client electronic devices (e.g., ACD client electronic devices 28, 30, 32, 34) and ACD compute system 12 may form modular ACD system 54.

The Automated Clinical Documentation System

Figure 2:
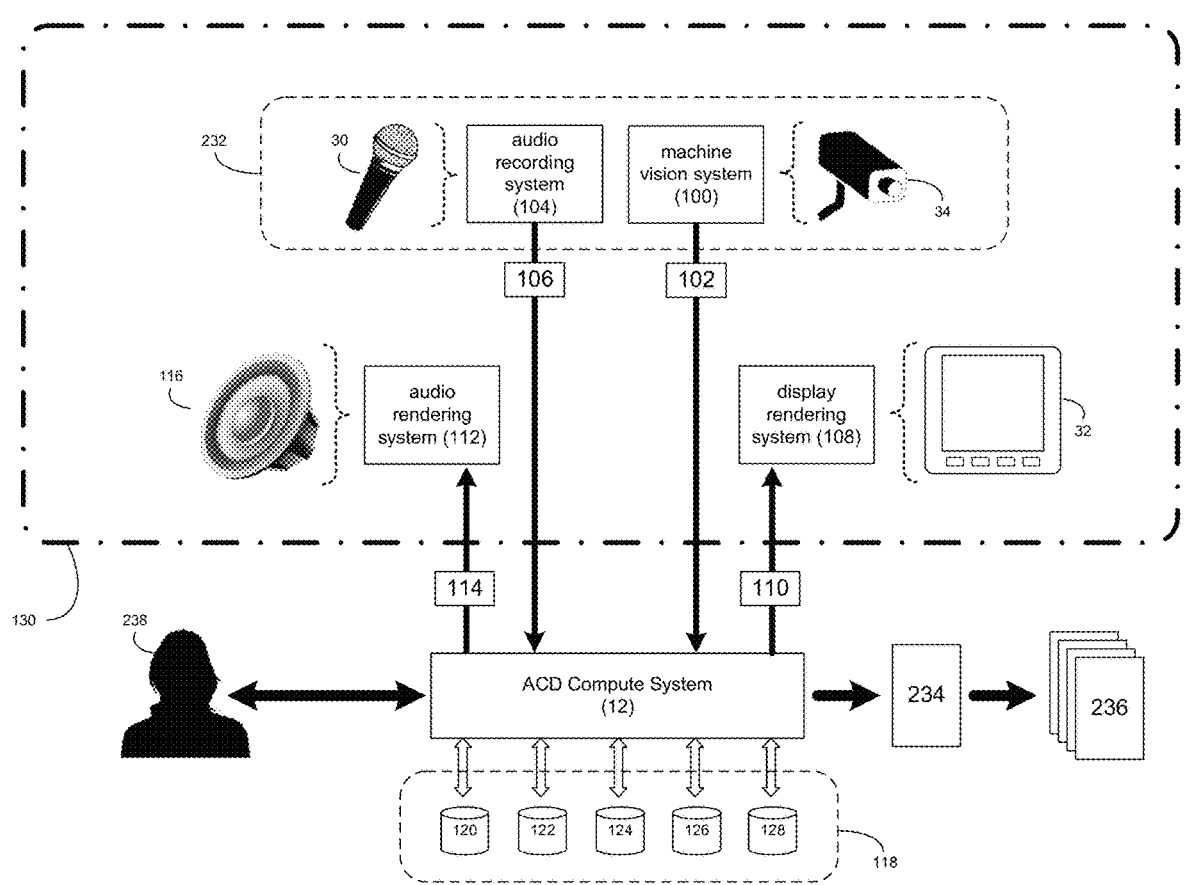
FIG. 2 is a diagrammatic view of a modular ACD system incorporating the automated clinical documentation compute system of FIG. 1.

Referring also to FIG. 2, there is shown a simplified exemplary embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a compute system (e.g., ACD compute system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD compute system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone (e.g., one example of a body worn microphone), a lapel microphone (e.g., another example of a body worn microphone), an embedded microphone, such as those embedded within eyeglasses, smart phones, tablet computers and/or watches (e.g., another example of a body worn microphone), and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118 are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD compute system 12 may include a plurality of discrete compute systems. As discussed above, ACD compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD compute system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Microphone Array

Figure 3:
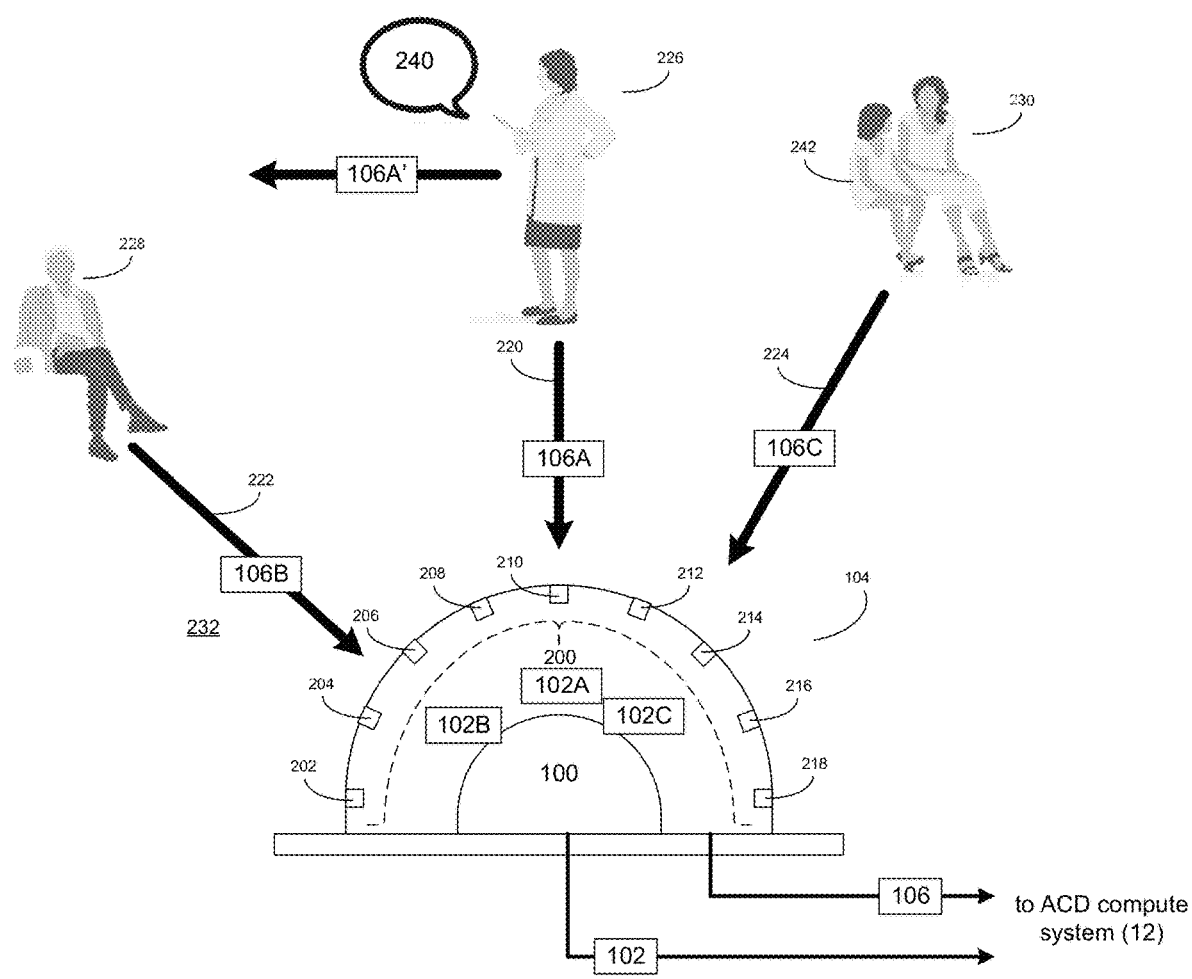
FIG. 3 is a diagrammatic view of a mixed-media ACD device included within the modular ACD system of FIG. 2.

Referring also to FIG. 3, audio recording system 104 may include microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACD system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACD system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230). Further, modular ACD system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference. In particular, null-steering precoding may be a method of beamforming for narrowband signals that may compensate for delays of receiving signals from a specific source at different elements of an antenna array. In general and to improve performance of the antenna array, incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically and as will be discussed below in greater detail, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD compute system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD compute system 12 may be included within mixed-media ACD device 232 or external to mixed-media ACD device 232.

The Automated Clinical Documentation Process

As discussed above, ACD compute system 12 may execute all or a portion of automated clinical documentation process 10, wherein the instruction sets and subroutines of automated clinical documentation process 10 (which may be stored on one or more of e.g., storage devices 16, 20, 22, 24, 26) may be executed by ACD compute system 12 and/or one or more of ACD client electronic devices 28, 30, 32, 34.

Figure 4:
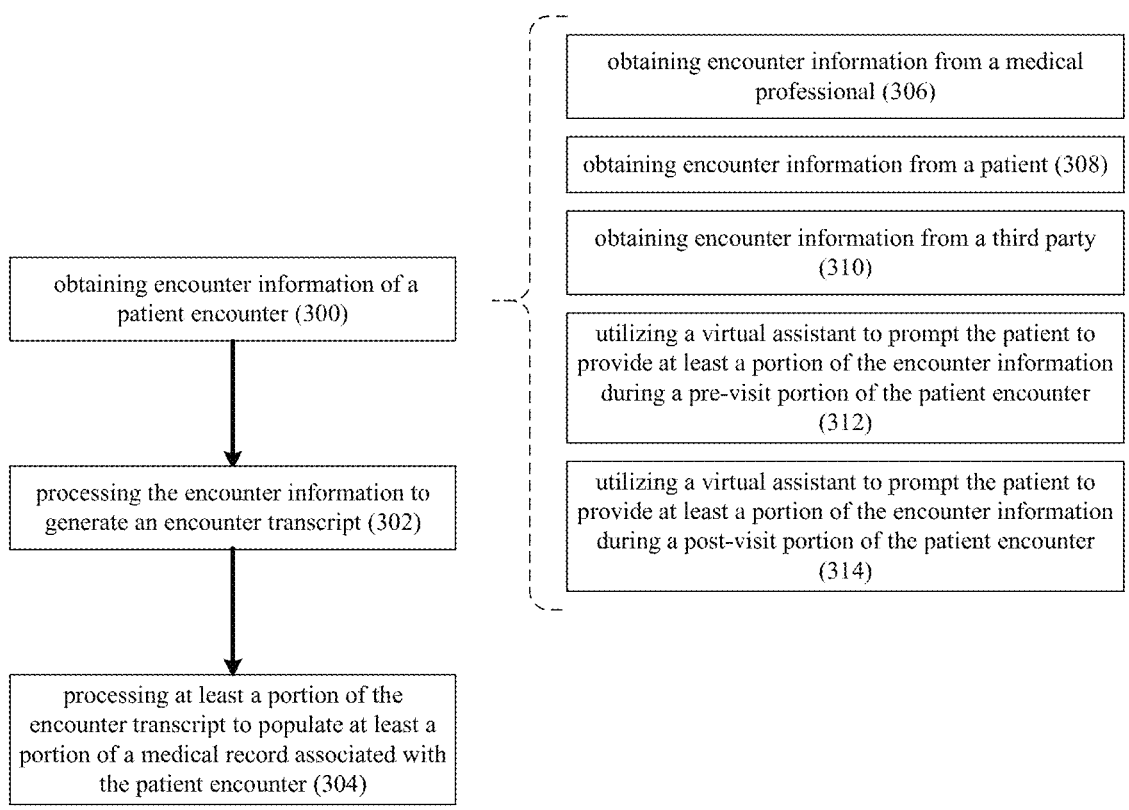
FIG. 4 is a flow chart of one implementation of the automated clinical documentation process of FIG. 1.

As discussed above, automated clinical documentation process 10 may be configured to automate the collection and processing of clinical encounter information to generate/store/distribute medical records. Accordingly and referring also to FIG. 4, automated clinical documentation process 10 may be configured to obtain 300 encounter information (e.g., machine vision encounter information 102 and/or audio encounter information 106) of a patient encounter (e.g., a visit to a doctor's office). Automated clinical documentation process 10 may further be configured to process 302 the encounter information (e.g., machine vision encounter information 102 and/or audio encounter information 106) to generate an encounter transcript (e.g., encounter transcript 234), wherein automated clinical documentation process 10 may then process 304 at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

For example, assume that a patient (e.g., encounter participant 228) visits a clinical environment (e.g., a doctor's office) because they do not feel well. They have a headache, fever, chills, a cough, and some difficulty breathing. In this particular example, a monitored space (e.g., monitored space 130) within the clinical environment (e.g., the doctor's office) may be outfitted with machine vision system 100 configured to obtain machine vision encounter information 102 concerning the patient encounter (e.g., encounter participant 228 visiting the doctor's office) and audio recording system 104 configured to obtain audio encounter information 106 concerning the patient encounter (e.g., encounter participant 228 visiting the doctor's office) via one or more audio sensors (e.g., audio acquisition devices 202, 204, 206, 208, 210, 212, 214, 216, 218).

As discussed above, machine vision system 100 may include a plurality of discrete machine vision systems if the monitored space (e.g., monitored space 130) within the clinical environment (e.g., the doctor's office) is larger or a higher level of resolution is desired, wherein examples of machine vision system 100 may include but are not limited to: an RGB imaging system, an infrared imaging system, an ultraviolet imaging system, a laser imaging system, a SONAR imaging system, a RADAR imaging system, and a thermal imaging system. Accordingly and in certain instances/embodiments, machine vision system 100 may include one or more of each of an RGB imaging system, an infrared imaging system, an ultraviolet imaging system, a laser imaging system, a SONAR imaging system, a RADAR imaging system, and a thermal imaging system positioned throughout monitored space 130, wherein each of these systems may be configured to provide data (e.g., machine vision encounter information 102) to ACD compute system 12 and/or modular ACD system 54.

As also discussed above, audio recording system 104 may include a plurality of discrete audio recording systems if the monitored space (e.g., monitored space 130) within the clinical environment (e.g., the doctor's office) is larger or a higher level of resolution is desired, wherein examples of audio recording system 104 may include but are not limited to: a handheld microphone, a lapel microphone, an embedded microphone (such as those embedded within eyeglasses, smart phones, tablet computers and/or watches) and an audio recording device. Accordingly and in certain instances/embodiments, audio recording system 104 may include one or more of each of a handheld microphone, a lapel microphone, an embedded microphone (such as those embedded within eyeglasses, smart phones, tablet computers and/or watches) and an audio recording device positioned throughout monitored space 130, wherein each of these microphones/devices may be configured to provide data (e.g., audio encounter information 106) to ACD compute system 12 and/or modular ACD system 54.

Since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and via machine vision encounter information 102, visual speech recognition (via visual lip reading functionality) may be utilized by automated clinical documentation process 10 to further effectuate the gathering of audio encounter information 106.

Accordingly and when obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

When automated clinical documentation process 10 obtains 300 the encounter information, automated clinical documentation process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

Further and when automated clinical documentation process 10 obtains 300 encounter information, automated clinical documentation process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office).

Automated Transcript Generation

Automated clinical documentation process 10 may be configured to process the encounter information (e.g., machine vision encounter information 102 and/or audio encounter information 106) to generate encounter transcript 234 that may be automatically formatted and punctuated.

Figure 5:
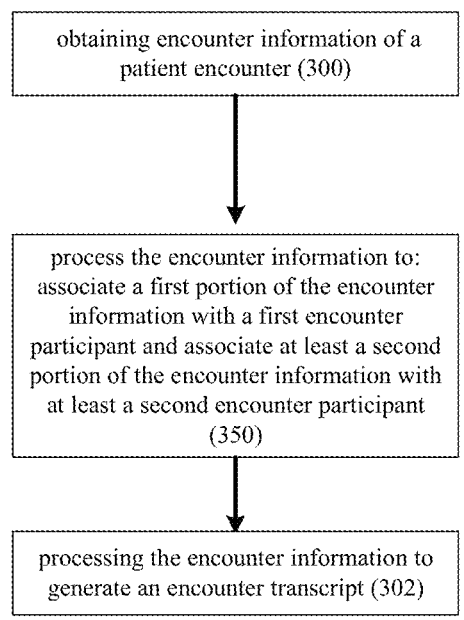
FIG. 5 is a flow chart of another implementation of the automated clinical documentation process of FIG. 1.

Accordingly and referring also to FIG. 5, automated clinical documentation process 10 may be configured to obtain 300 encounter information (e.g., machine vision encounter information 102 and/or audio encounter information 106) of a patient encounter (e.g., a visit to a doctor's office).

Automated clinical documentation process 10 may process 350 the encounter information (e.g., machine vision encounter information 102 and/or audio encounter information 106) to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant.

As discussed above, modular ACD system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACD system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACD system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly, automated clinical documentation process 10 may process 350 the encounter information (e.g., machine vision encounter information 102 and/or audio encounter information 106) to: associate a first portion (e.g., encounter information 106A) of the encounter information (e.g., audio encounter information 106) with a first encounter participant (e.g., encounter participant 226), and associate at least a second portion (e.g., encounter information 106B, 106C) of the encounter information (e.g., audio encounter information 106) with at least a second encounter participant (e.g., encounter participants 228, 230; respectively).

Further and when processing 350 the encounter information (e.g., audio encounter information 106A, 106B, 106C), automated clinical documentation process 10 may compare each of audio encounter information 106A, 106B, 106C to the voice prints defined within the above-referenced voice print datasource so that the identity of encounter participants 226, 228, 230 (respectively) may be determined. Accordingly, if the voice print datasource includes a voice print that corresponds to one or more of the voice of encounter participant 226 (as heard within audio encounter information 106A), the voice of encounter participant 228 (as heard within audio encounter information 106B) or the voice of encounter participant 230 (as heard within audio encounter information 106C), the identity of one or more of encounter participants 226, 228, 230 may be defined. And in the event that a voice heard within one or more of audio encounter information 106A, audio encounter information 106B or audio encounter information 106C is unidentifiable, that one or more particular encounter participant may be defined as "Unknown Participant".

Once the voices of encounter participants 226, 228, 230 are processed 350, automated clinical documentation process 10 may generate 302 an encounter transcript (e.g., encounter transcript 234) based, at least in part, upon the first portion of the encounter information (e.g., audio encounter information 106A) and the at least a second portion of the encounter information (e.g., audio encounter information 106B. 106C).

Automated Role Assignment

Automated clinical documentation process 10 may be configured to automatically define roles for the encounter participants (e.g., encounter participants 226, 228, 230) in the patient encounter (e.g., a visit to a doctor's office).

Figure 6:
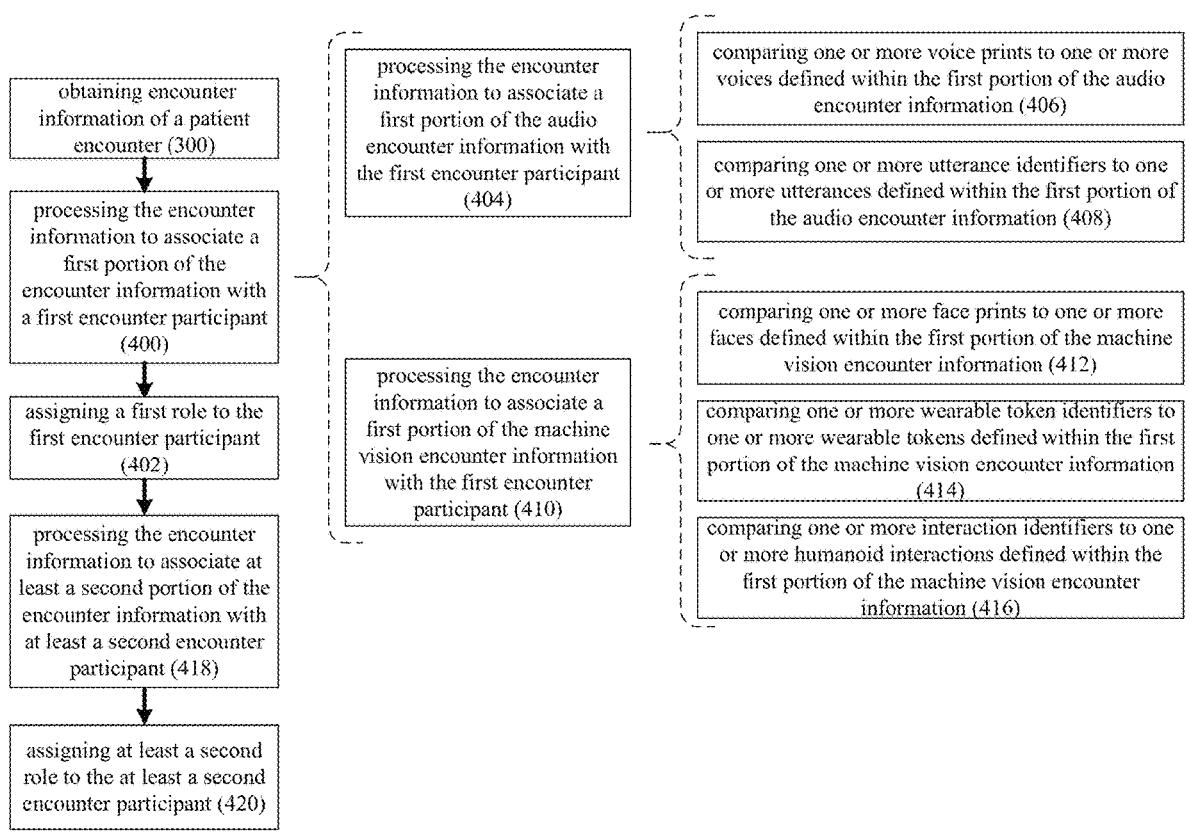
FIG. 6 is a flow chart of another implementation of the automated clinical documentation process of FIG. 1.

Accordingly and referring also to FIG. 6, automated clinical documentation process 10 may be configured to obtain 300 encounter information (e.g., machine vision encounter information 102 and/or audio encounter information 106) of a patient encounter (e.g., a visit to a doctor's office).

Automated clinical documentation process 10 may then process 400 the encounter information (e.g., machine vision encounter information 102 and/or audio encounter information 106) to associate a first portion of the encounter information with a first encounter participant (e.g., encounter participant 226) and assign 402 a first role to the first encounter participant (e.g., encounter participant 226).

When processing 400 the encounter information (e.g., machine vision encounter information 102 and/or audio encounter information 106) to associate the first portion of the encounter information with the first encounter participant (e.g., encounter participant 226), automated clinical documentation process 10 may process 404 the encounter information (e.g., machine vision encounter information 102 and/or audio encounter information 106) to associate a first portion of the audio encounter information (e.g., audio encounter information 106A) with the first encounter participant (e.g., encounter participant 226).

Specifically and when processing 404 the encounter information (e.g., machine vision encounter information 102 and/or audio encounter information 106) to associate the first portion of the audio encounter information (e.g., audio encounter information 106A) with the first encounter participant (e.g., encounter participant 226), automated clinical documentation process 10 may compare 406 one or more voice prints (defined within voice print datasource) to one or more voices defined within the first portion of the audio encounter information (e.g., audio encounter information 106A); and may compare 408 one or more utterance identifiers (defined within utterance datasource) to one or more utterances defined within the first portion of the audio encounter information (e.g., audio encounter information 106A); wherein comparisons 406, 408 may allow automated clinical documentation process 10 to assign 402 a first role to the first encounter participant (e.g., encounter participant 226). For example, if the identity of encounter participant 226 can be defined via voice prints, a role for encounter participant 226 may be assigned 402 if that identity defined is associated with a role (e.g., the identity defined for encounter participant 226 is Doctor Susan Jones). Further, if an utterance made by encounter participant 226 is "I am Doctor Susan Jones", this utterance may allow a role for encounter participant 226 to be assigned 402.

When processing 400 the encounter information (e.g., machine vision encounter information 102 and/or audio encounter information 106) to associate the first portion of the encounter information with the first encounter participant (e.g., encounter participant 226), automated clinical documentation process 10 may process 410 the encounter information (e.g., machine vision encounter information 102 and/or audio encounter information 106) to associate a first portion of the machine vision encounter information (e.g., machine vision encounter information 102A) with the first encounter participant (e.g., encounter participant 226).

Specifically and when processing 410 the encounter information (e.g., machine vision encounter information 102 and/or audio encounter information 106) to associate the first portion of the machine vision encounter information (e.g., machine vision encounter information 102A) with the first encounter participant (e.g., encounter participant 226), automated clinical documentation process 10 may compare 412 one or more face prints (defined within face print datasource) to one or more faces defined within the first portion of the machine vision encounter information (e.g., machine vision encounter information 102A); compare 414 one or more wearable token identifiers (defined within wearable token identifier datasource) to one or more wearable tokens defined within the first portion of the machine vision encounter information (e.g., machine vision encounter information 102A); and compare 416 one or more interaction identifiers (defined within interaction identifier datasource) to one or more humanoid interactions defined within the first portion of the machine vision encounter information (e.g., machine vision encounter information 102A); wherein comparisons 412, 414, 416 may allow automated clinical documentation process 10 to assign 402 a first role to the first encounter participant (e.g., encounter participant 226). For example, if the identity of encounter participant 226 can be defined via face prints, a role for encounter participant 226 may be assigned 402 if that identity defined is associated with a role (e.g., the identity defined for encounter participant 226 is Doctor Susan Jones). Further, if a wearable token worn by encounter participant 226 can be identified as a wearable token assigned to Doctor Susan Jones, a role for encounter participant 226 may be assigned 402. Additionally, if an interaction made by encounter participant 226 corresponds to the type of interaction that is made by a doctor, the existence of this interaction may allow a role for encounter participant 226 to be assigned 402.

Examples of such wearable tokens may include but are not limited to wearable devices that may be worn by the medical professionals when they are within monitored space 130 (or after they leave monitored space 130). For example, these wearable tokens may be worn by medical professionals when e.g., they are moving between monitored rooms within monitored space 130, travelling to and/or from monitored space 130, and/or outside of monitored space 130 (e.g., at home).

Additionally, automated clinical documentation process 10 may process 418 the encounter information (e.g., machine vision encounter information 102 and/or audio encounter information 106) to associate at least a second portion of the encounter information with at least a second encounter participant; and may assign 420 at least a second role to the at least a second encounter participant.

Specifically, automated clinical documentation process 10 may process 418 the encounter information (e.g., machine vision encounter information 102 and/or audio encounter information 106) to associate at least a second portion of the encounter information with at least a second encounter participant. For example, automated clinical documentation process 10 may process 418 the encounter information (e.g., machine vision encounter information 102 and/or audio encounter information 106) to associate audio encounter information 106B and machine vision encounter information 102B with encounter participant 228 and may associate audio encounter information 106C and machine vision encounter information 102C with encounter participant 230.

Further, automated clinical documentation process 10 may assign 420 at least a second role to the at least a second encounter participant. For example, automated clinical documentation process 10 may assign 420 a role to encounter participants 228, 230.

Automated Movement Tracking

Automated clinical documentation process 10 may be configured to track the movement and/or interaction of humanoid shapes within the monitored space (e.g., monitored space 130) during the patient encounter (e.g., a visit to a doctor's office) so that e.g., the automated clinical documentation process 10 knows when encounter participants (e.g., one or more of encounter participants 226, 228, 230) enter, exit or cross paths within monitored space 130.

Figure 7:
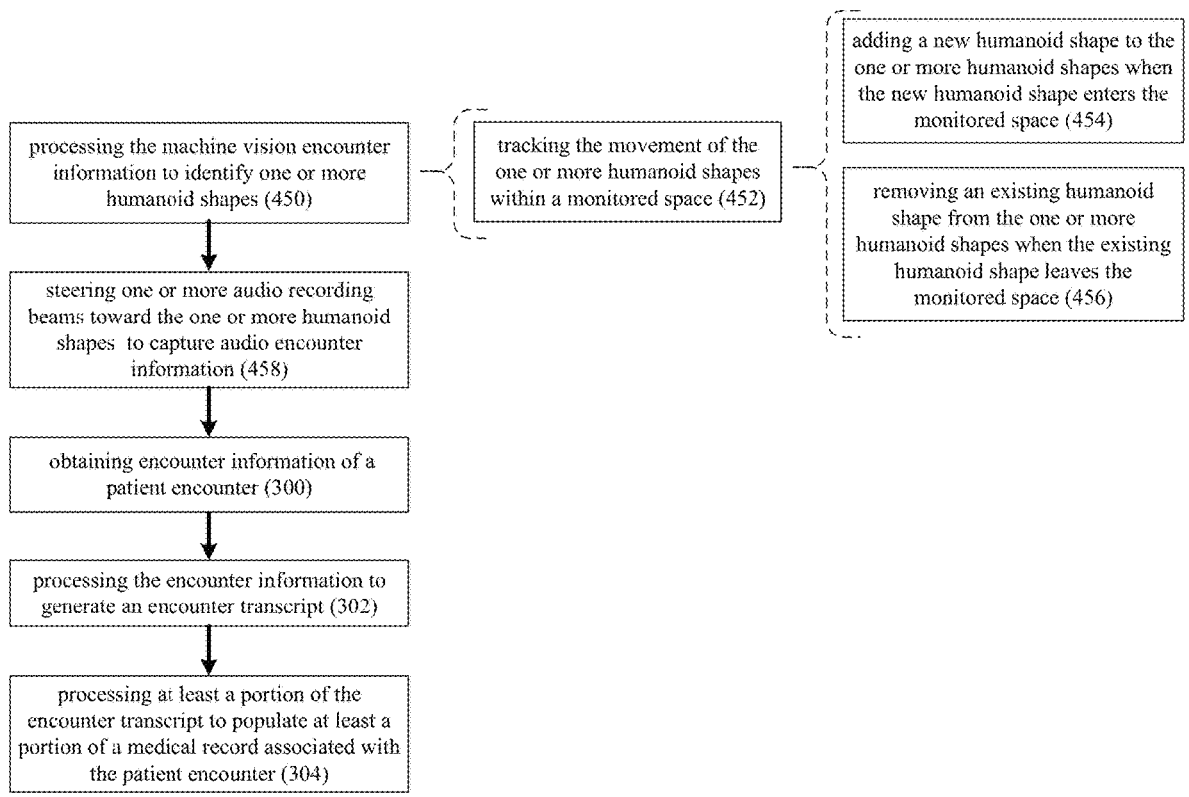
FIG. 7 is a flow chart of another implementation of the automated clinical documentation process of FIG. 1.

Accordingly and referring also to FIG. 7, automated clinical documentation process 10 may process 450 the machine vision encounter information (e.g., machine vision encounter information 102) to identify one or more humanoid shapes. As discussed above, examples of machine vision system 100 generally (and ACD client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

When ACD client electronic device 34 includes a visible light imaging system (e.g., an RGB imaging system), ACD client electronic device 34 may be configured to monitor various objects within monitored space 130 by recording motion video in the visible light spectrum of these various objects. When ACD client electronic device 34 includes an invisible light imaging systems (e.g., a laser imaging system, an infrared imaging system and/or an ultraviolet imaging system), ACD client electronic device 34 may be configured to monitor various objects within monitored space 130 by recording motion video in the invisible light spectrum of these various objects. When ACD client electronic device 34 includes an X-ray imaging system, ACD client electronic device 34 may be configured to monitor various objects within monitored space 130 by recording energy in the X-ray spectrum of these various objects. When ACD client electronic device 34 includes a SONAR imaging system, ACD client electronic device 34 may be configured to monitor various objects within monitored space 130 by transmitting soundwaves that may be reflected off of these various objects. When ACD client electronic device 34 includes a RADAR imaging system, ACD client electronic device 34 may be configured to monitor various objects within monitored space 130 by transmitting radio waves that may be reflected off of these various objects. When ACD client electronic device 34 includes a thermal imaging system, ACD client electronic device 34 may be configured to monitor various objects within monitored space 130 by tracking the thermal energy of these various objects.

As discussed above, ACD compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly and when processing 450 the machine vision encounter information (e.g., machine vision encounter information 102) to identify one or more humanoid shapes, automated clinical documentation process 10 may be configured to compare the humanoid shapes defined within one or more datasources 118 to potential humanoid shapes within the machine vision encounter information (e.g., machine vision encounter information 102).

When processing 450 the machine vision encounter information (e.g., machine vision encounter information 102) to identify one or more humanoid shapes, automated clinical documentation process 10 may track 452 the movement of the one or more humanoid shapes within the monitored space (e.g., monitored space 130). For example and when tracking 452 the movement of the one or more humanoid shapes within monitored space 130, automated clinical documentation process 10 may add 454 a new humanoid shape to the one or more humanoid shapes when the new humanoid shape enters the monitored space (e.g., monitored space 130) and/or may remove 456 an existing humanoid shape from the one or more humanoid shapes when the existing humanoid shape leaves the monitored space (e.g., monitored space 130).

For example, assume that a lab technician (e.g., encounter participant 242) temporarily enters monitored space 130 to chat with encounter participant 230. Accordingly, automated clinical documentation process 10 may add 454 encounter participant 242 to the one or more humanoid shapes being tracked 452 when the new humanoid shape (i.e., encounter participant 242) enters monitored space 130. Further, assume that the lab technician (e.g., encounter participant 242) leaves monitored space 130 after chatting with encounter participant 230. Therefore, automated clinical documentation process 10 may remove 456 encounter participant 242 from the one or more humanoid shapes being tracked 452 when the humanoid shape (i.e., encounter participant 242) leaves monitored space 130.

Also and when tracking 452 the movement of the one or more humanoid shapes within monitored space 130, automated clinical documentation process 10 may monitor the trajectories of the various humanoid shapes within monitored space 130. Accordingly, assume that when leaving monitored space 130, encounter participant 242 walks in front of (or behind) encounter participant 226. As automated clinical documentation process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by automated clinical documentation process 10.

Automated clinical documentation process 10 may be configured to obtain 300 the encounter information of the patient encounter (e.g., a visit to a doctor's office), which may include machine vision encounter information 102 (in the manner described above) and/or audio encounter information 106.

Automated clinical documentation process 10 may steer 458 one or more audio recording beams (e.g., audio recording beams 220, 222, 224) toward the one or more humanoid shapes (e.g., encounter participants 226, 228, 230) to capture audio encounter information (e.g., audio encounter information 106), wherein audio encounter information 106 may be included within the encounter information (e.g., machine vision encounter information 102 and/or audio encounter information 106).

Specifically and as discussed above, automated clinical documentation process 10 (via modular ACD system 54 and/or audio recording system 104) may utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACD system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACD system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Once obtained, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Automated Amendment of Records

Figure 8:
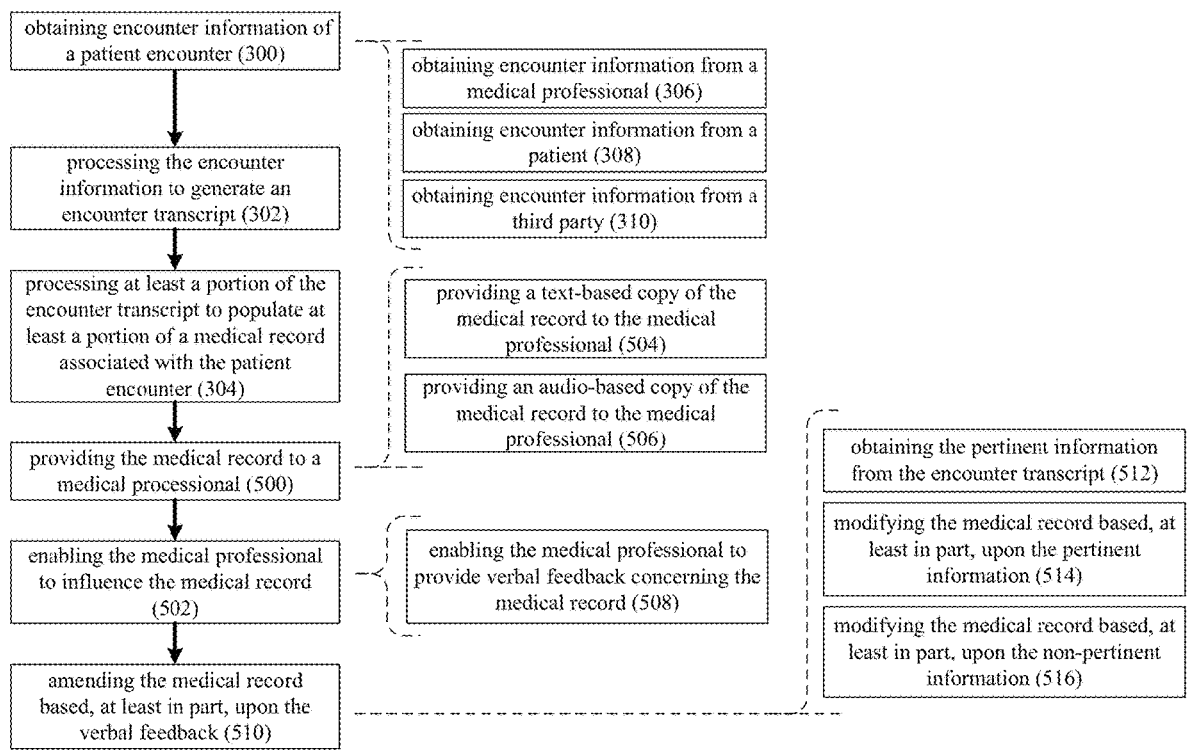
FIG. 8 is a flow chart of another implementation of the automated clinical documentation process of FIG. 1.

Automated clinical documentation process 10 may be configured to allow a user (e.g., a medical professional) to amend medical record 236 based upon verbal feedback received from the user (e.g., a medical professional). Accordingly and referring also to FIG. 8, automated clinical documentation process 10 may be configured to obtain 300 encounter information of a patient encounter (e.g., a visit to a doctor's office), wherein (and as discussed above) this encounter information may include machine vision encounter information 102 and/or audio encounter information 106.

As discussed above and when obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230).

Further and as discussed above, automated clinical documentation process 10 may be configured to process 302 the encounter information (e.g., machine vision encounter information 102 and/or audio encounter information 106) to generate an encounter transcript (e.g., encounter transcript 234). Once the encounter transcript (e.g., encounter transcript 234) is generated, automated clinical documentation process 10 may process 304 at least a portion of the encounter transcript (e.g., encounter transcript 234) to populate at least a portion of a medical record (e.g., medical record 236) associated with the patient encounter (e.g., the visit to the doctor's office).

As discussed above, encounter transcript 234 and/or medical record 236 may be reviewed by a medical professional involved with the patient encounter (e.g., a visit to a doctor's office) to determine the accuracy of the same and/or make corrections to the same. For example, a scribe involved with (or assigned to) the patient encounter (e.g., a visit to a doctor's office) and/or a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated with the participants of the patient encounter) to enhance the future accuracy/efficiency/performance of automated clinical documentation process 10.

Accordingly and to effectuate such a review of medical record 236, automated clinical documentation process 10 may provide 500 the medical record (e.g., medical record 236) to a medical professional (e.g., encounter participant 226) and may enable 502 the medical professional (e.g., encounter participant 226) to influence the medical record (e.g., medical record 236).

When providing 500 the medical record (e.g., medical record 236) to a medical professional (e.g., encounter participant 226), automated clinical documentation process 10 may: provide 504 a text-based copy of the medical record (e.g., medical record 236) to the medical professional (e.g., encounter participant 226); and/or provide 506 an audio-based copy of the medical record (e.g., medical record 236) to the medical professional (e.g., encounter participant 226).

For example, automated clinical documentation process 10 may provide 504 a text-based copy (e.g., a printed hardcopy or a computer rendered softcopy) of medical record 236 so that medical record 236 may be reviewed for accuracy by the medical professional (e.g., encounter participant 226). Additionally/alternatively, automated clinical documentation process 10 may provide 506 an audio-based copy (e.g., via an audio stream) of medical record 236 so that medical record 236 may be reviewed for accuracy by the medical professional (e.g., encounter participant 226).

When enabling 502 the medical professional (e.g., encounter participant 226) to influence the medical record (e.g., medical record 236), automated clinical documentation process 10 may enable 508 the medical professional (e.g., encounter participant 226) to provide verbal feedback (e.g., feedback 240) concerning the medical record (e.g., medical record 236). Accordingly and if reading a text-based copy of the medical record (e.g., medical record 236), automated clinical documentation process 10 may "listen" for verbal feedback 240 via e.g., audio input device 30 and/or the plurality of discrete audio acquisition devices (e.g., audio acquisition devices 202, 204, 206, 208, 210, 212, 214, 216, 218). Additionally/alternatively and if listening to an audio-based copy of the medical record (e.g., medical record 236), automated clinical documentation process 10 may "listen" for verbal feedback 240 via e.g., audio input device 30 and/or the plurality of discrete audio acquisition devices (e.g., audio acquisition devices 202, 204, 206, 208, 210, 212, 214, 216, 218).

Once verbal feedback 240 is received, automated clinical documentation process 10 may amend 510 the medical record (e.g., medical record 236), based, at least in part, upon verbal feedback 240. As will be discussed below in greater detail, verbal feedback 204 may concern adding pertinent information included within the encounter transcript (e.g., encounter transcript 234) into the medical record (e.g., medical record 236). Conversely, verbal feedback 204 may concern removing non-pertinent information from the medical record (e.g., medical record 236).

If verbal feedback 240 concerns including pertinent information in the medical record (e.g., medical record 236); amending 510 the medical record (e.g., medical record 236) based, at least in part, upon verbal feedback 240 may include: obtaining 512 the pertinent information from the encounter transcript (e.g., encounter transcript 234); and modifying 514 the medical record (e.g., medical record 236) based, at least in part, upon the pertinent information obtained 512. Alternatively and if verbal feedback 240 concerns removing non-pertinent information from the medical record (e.g., medical record 236); amending 510 the medical record (e.g., medical record 236) based, at least in part, upon verbal feedback 240 may include: modifying 516 the medical record (e.g., medical record 236) based, at least in part, upon the non-pertinent information.

Assume for this example that the medical professional (e.g., encounter participant 226) reviewed the medical record (e.g., medical record 236) and provided verbal feedback 240 concerning medical record 236. Verbal feedback 240 may be processed by automated clinical documentation process 10 using Natural Language Understanding (NLU) technology, such as that offered by Nuance Communications of Burlington, MA As is known in the art, NLU is a branch of artificial intelligence (AI) that uses computer software to understand input provided by humans in the form of sentences in text or speech format, thus allowing human-computer interaction (HCI). Specifically, NLU understanding of natural human languages enables computers to understand commands without the formalized syntax of computer languages and enables computers to communicate back to humans in their own languages. The field of NLU is typically considered to be a subset of natural language processing (NLP). While both NLU and NLP understand human language, NLU may more effectively communicate with untrained individuals and may better understand the intent and meaning of that human language. NLU may even understand the meaning of human language despite common human errors (e.g., mispronunciations, transposed letters/words, etc.). NLU uses AI algorithms to reduce human speech into a structured ontology, wherein these AI algorithms may extract content concerning intent, timing, locations and sentiments. For example and when processing a request for an island camping trip on Vancouver Island on the 18th of August, NLU may break down this request into subcomponents such as: need: ferry tickets [intent]/need: camping lot reservation [intent]/Vancouver Island [location]/August 18th [date].

Verbal feedback 240 provided by the medical professional (e.g., encounter participant 226) may concern simple administrative procedures, such as e.g., making minor edits to medical record 236 and/or adding/removing/revising a few words within medical record 236. However, verbal feedback 240 may involve more complex operations.

For example, assume that during the patient encounter (e.g., encounter participant 228 visiting the doctor's office), the medical professional (e.g., encounter participant 226) and the patient (e.g., encounter participant 228) discuss various things. Assume for illustrative purposes that one of this things discussed is that encounter participant 228 is constantly thirsty. However and upon reviewing medical record 236, the medical professional (e.g., encounter participant 226) realizes that the information and discussion concerning the constant thirst of encounter participant 228 is not included/referenced within medical record 236. Further, assume that the medical professional (e.g., encounter participant 226) believes that the information & discussion concerning the constant thirst of encounter participant 228 should have been included/referenced within medical record 236.

Accordingly, verbal feedback 240 provided by the medical professional (e.g., encounter participant 226) may be "Please include the discussion about the constant thirst of the patient". As discussed above, automated clinical documentation process 10 may amend 510 the medical record (e.g., medical record 236), based, at least in part, upon verbal feedback 240. Specifically and since verbal feedback 240 concerns including pertinent information (e.g., the information about the constant thirst of the patient) in the medical record (e.g., medical record 236); when amending 510 the medical record (e.g., medical record 236) based, at least in part, upon verbal feedback 240, automated clinical documentation process 10 may: obtain 512 the pertinent information (e.g., the information about the constant thirst of the patient) from the encounter transcript (e.g., encounter transcript 234); and may modify 514 the medical record (e.g., medical record 236) based, at least in part, upon the pertinent information obtained 512.

When modifying 514 the medical record (e.g., medical record 236) based, at least in part, upon the pertinent information obtained 512, automated clinical documentation process 10 may simply add the pertinent information (e.g., the information about the constant thirst of the patient) to the medical record (e.g., medical record 236). However, more substantial changes may occur to the medical record (e.g., medical record 236). For example, assume that the pertinent information (e.g., the information about the constant thirst of the patient) triggers a concern that to the patient (e.g., encounter participant 228) may be diabetic. Accordingly, automated clinical documentation process 10 may e.g., reformat the medical record (e.g., medical record 236) or may utilize a different template to generate the medical record (e.g., medical record 236).

Continuing with the above-stated example, further assume that during the patient encounter (e.g., encounter participant 228 visiting the doctor's office), the medical professional (e.g., encounter participant 226) and the patient (e.g., encounter participant 228) discussed that encounter participant 228 has lost three pounds. And upon reviewing medical record 236, the medical professional (e.g., encounter participant 226) realizes that the information and discussion concerning this loss of three pounds of encounter participant 228 is included/referenced within medical record 236. Further, assume that the medical professional (e.g., encounter participant 226) believes that the information and discussion concerning this loss of three pounds of encounter participant 228 should not have been included/referenced within medical record 236, as the patient (e.g., encounter participant 228) is more than 100 pounds overweight.

Accordingly, verbal feedback 240 provided by the medical professional (e.g., encounter participant 226) may be "Please remove the discussion about the loss of three pounds". As discussed above, automated clinical documentation process 10 may amend 510 the medical record (e.g., medical record 236), based, at least in part, upon verbal feedback 240. Specifically and since verbal feedback 240 concerns removing non-pertinent information from the medical record (e.g., medical record 236); amending 510 the medical record (e.g., medical record 236) based, at least in part, upon verbal feedback 240 may include modifying 516 the medical record (e.g., medical record 236) based, at least in part, upon the non-pertinent information (e.g., the loss of three pounds).

When modifying 516 the medical record (e.g., medical record 236) based, at least in part, upon the non-pertinent information, automated clinical documentation process 10 may simply remove the non-pertinent information (e.g., the information about the loss of three pounds) from the medical record (e.g., medical record 236). However, more substantial changes may occur to the medical record (e.g., medical record 236). For example, assume that the removal of the non-pertinent information (e.g., the loss of three pounds) triggers a concern that the weight of the patient is not under control. Accordingly, automated clinical documentation process 10 may e.g., reformat the medical record (e.g., medical record 236) or may utilize a different template to generate the medical record (e.g., medical record 236).

Tracking Procedural Events

Figure 9:
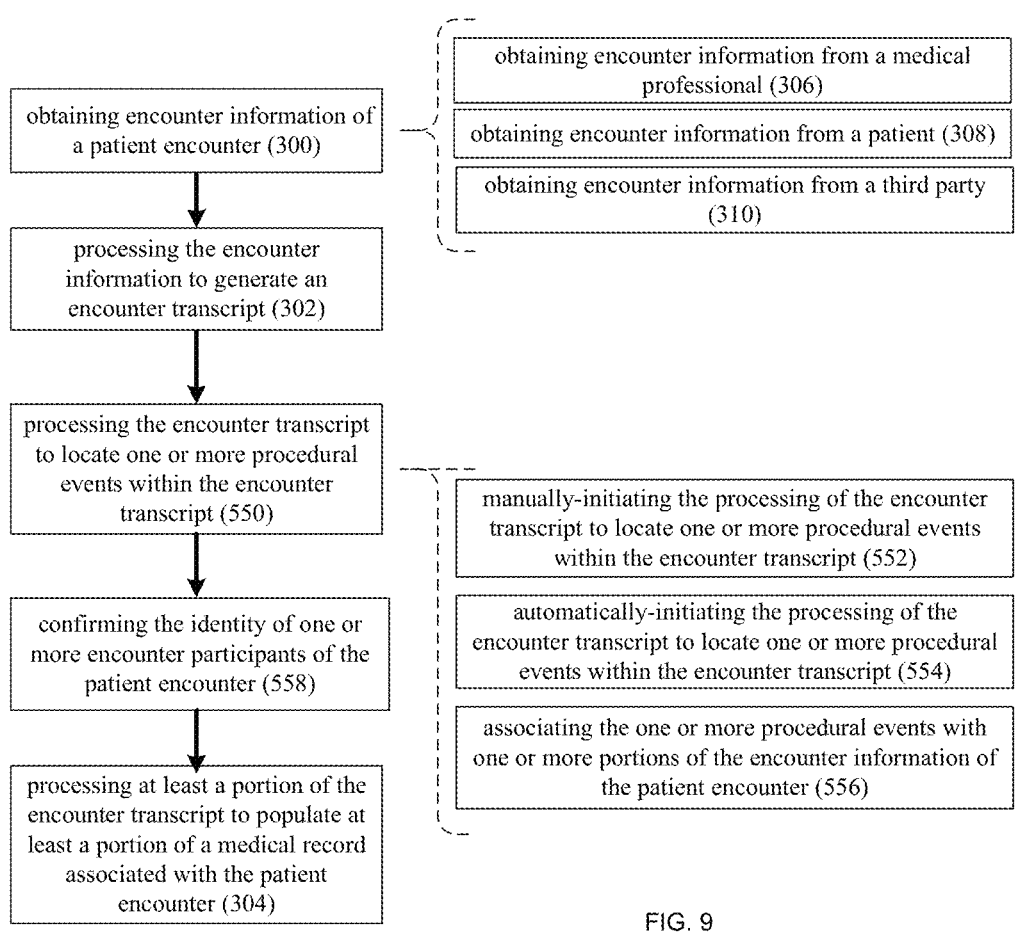
FIG. 9 is a flow chart of another implementation of the automated clinical documentation process of FIG. 1.

Automated clinical documentation process 10 may be configured to allow a user (e.g., a medical professional) to examine an encounter transcript (e.g., encounter transcript 234) for the occurrence of certain procedural events. Accordingly and referring also to FIG. 9, automated clinical documentation process 10 may be configured to obtain 300 encounter information of a patient encounter (e.g., a visit to a doctor's office), wherein (and as discussed above) this encounter information may include machine vision encounter information 102 and/or audio encounter information 106.

As discussed above and when obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230).

Further and as discussed above, automated clinical documentation process 10 may be configured to process 302 the encounter information (e.g., machine vision encounter information 102 and/or audio encounter information 106) to generate an encounter transcript (e.g., encounter transcript 234). Once the encounter transcript (e.g., encounter transcript 234) is generated, automated clinical documentation process 10 may process 304 at least a portion of the encounter transcript (e.g., encounter transcript 234) to populate at least a portion of a medical record (e.g., medical record 236) associated with the patient encounter (e.g., the visit to the doctor's office).

Automated clinical documentation process 10 may process 550 the encounter transcript (e.g., encounter transcript 234) to locate one or more procedural events within the encounter transcript (e.g., encounter transcript 234). Examples of such procedural events may include but are not limited to: an informed consent event; a personal medical history event; a family medical history event; a drug allergy event; a drug side-effect event; and a drug warning event.

> Informed Consent Event: When procedures are performed on patients, the patients may be required to give an informed consent with respect to the procedures being performed. Accordingly and in the event that e.g., a patient is receiving an injectable medication, the patient may be required to provide an informed consent to the medical professional authorizing the injection.
>
> Personal Medical History Event: When a patient visits a clinical environment, the medical professional may inquire about the personal medical history of the patient, as such information may be of paramount importance when determining how to examine and/or treat the patient.
>
> Family Medical History Event: When a patient visits a clinical environment, the medical professional may inquire about the family medical history of the patient, as such information may be of paramount importance when determining how to examine and/or treat the patient.
>
> Drug Allergy Event: When a patient visits a clinical environment, the medical professional may inquire about any drug allergies that the patient has or may have, as such information may be of paramount importance when determining how to treat the patient.
>
> Drug Side-Effect Event: When a patient visits a clinical environment, the medical professional may explain to the patient any potential side effects that the patient may experience when taking a medication that has been/will be prescribed.
>
> Drug Warning Event: When a patient visits a clinical environment, the medical professional may explain to the patient any potential addictive effects that are associated with a medication that has been/will be prescribed.

When processing 550 the encounter transcript (e.g., encounter transcript 234) to locate one or more procedural events within the encounter transcript (e.g., encounter transcript 234), the processing 550 of the encounter transcript (e.g., encounter transcript 234) may be manually-initiated or automatically-initiated.

For example and via automated clinical documentation process 10, a medical professional (e.g., encounter participant 226) may manually-initiate 552 the processing 550 of the encounter transcript (e.g., encounter transcript 234) to locate one or more procedural events within the encounter transcript (e.g., encounter transcript 234). Accordingly and at the request of the medical professional (e.g., encounter participant 226), automated clinical documentation process 10 may process 550 encounter transcript 234 to look for portions of encounter transcript 234 that concern one or more of an informed consent event; a personal medical history event; a family medical history event; a drug allergy event; a drug side-effect event; and a drug warning event.

Additionally/alternatively, automated clinical documentation process 10 may automatically-initiate 554 the processing 550 of the encounter transcript (e.g., encounter transcript 234) to locate one or more procedural events within the encounter transcript (e.g., encounter transcript 234). Accordingly and automatically, automated clinical documentation process 10 may process 550 encounter transcript 234 to look for portions of encounter transcript 234 that concern one or more of an informed consent event; a personal medical history event; a family medical history event; a drug allergy event; a drug side-effect event; and a drug warning event.

Specifically and when processing 550 the encounter transcript (e.g., encounter transcript 234) to locate one or more procedural events within the encounter transcript (e.g., encounter transcript 234), automated clinical documentation process 10 may examine encounter transcript 234 to locate portions of encounter transcript 234 (using e.g., a defined vocabulary words, a list of words/phrases, artificial intelligence and/or machine learning) that concern one or more of an informed consent event; a personal medical history event; a family medical history event; a drug allergy event; a drug side-effect event; and a drug warning event.

Once the procedural events are located within the encounter transcript (e.g., encounter transcript 234), automated clinical documentation process 10 may associate 556 the one or more procedural events (e.g., an informed consent event; a personal medical history event; a family medical history event; a drug allergy event; a drug side-effect event; and/or a drug warning event) with one or more portions of the encounter information (e.g., machine vision encounter information 102 and/or audio encounter information 106) of the patient encounter (e.g., a visit to a doctor's office).

For example, if processing 550 the encounter transcript (e.g., encounter transcript 234) to locate an informed consent event concerning the administration of a flu vaccine, automated clinical documentation process 10 may examine encounter transcript 234 to locate the portion(s) of encounter transcript 234 that concern the administration of the flu vaccine. Once the relevant portion(s) of the encounter transcript 234 are located, automated clinical documentation process 10 may associate 556 the procedural event(s) located within encounter transcript 234 with one or more portions of the encounter information (e.g., machine vision encounter information 102 and/or audio encounter information 106), wherein these one or more portions of the encounter information (e.g., machine vision encounter information 102 and/or audio encounter information 106) may be video information (from e.g., machine vision encounter information 102) and/or audio information (from e.g., audio encounter information 106) that illustrates the patient in question providing the informed consent concerning the administration of the flu vaccine.

As discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Further and as discussed above, when processing audio encounter information 106, automated clinical documentation process 10 may compare audio encounter information 106 to the voice prints defined within the above-referenced voice print datasource so that the identity of encounter participants may be determined. Therefore, automated clinical documentation process 10 may confirm 558 the identity of one or more encounter participants of the patient encounter (e.g., encounter participant 228 visiting the doctor's office). For example, if the voice print datasource includes a voice print for encounter participant 228 (i.e., the patient visiting the doctor's office), automated clinical documentation process 10 may confirm 558 the identity of encounter participant 228, thus authenticating the informed consent given by encounter participant 228 concerning the administration of the flu vaccine.

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
    obtaining encounter information of a patient encounter, wherein the encounter information includes audio encounter information and machine vision encounter information,
    locating one or more procedural events, wherein at least one of the one or more procedural events includes an informed medical consent event for a medical procedure performed on a patient during the patient encounter;
    confirming an identity of one or more encounter participants of the patient encounter participating in the informed medical consent event using at least one of the audio encounter information and machine vision encounter information, wherein confirming the identity of one or more encounter participants of the patient encounter participating in the informed medical consent event includes at least one of:
        matching one or more voice characteristics of a recording of the audio encounter information to one or more data sources containing matching voice characteristics in a voice print,
        matching one or more facial characteristics of a recording of the machine vision encounter information to one or more data sources containing matching facial characteristics in a face print; and
    authenticating the informed medical consent event based upon, at least in part, confirming the identity of one or more encounter participants of the patient encounter participating in the informed medical consent event and locating the informed medical consent event for the medical procedure performed on the patient during the patient encounter.

2. The computer-implemented method of claim 1 wherein obtaining encounter information of a patient encounter includes one or more of:
    obtaining encounter information from a medical professional;
    obtaining encounter information from a patient; and
    obtaining encounter information from a third party.

3. The computer-implemented method of claim 1 further comprising:
    processing the audio encounter information of the encounter information to generate an encounter transcript; and
    processing at least a portion of the encounter transcript to populate at least a portion of a medical record associated with the patient encounter; and
    wherein locating the one or more procedural events includes locating the one or more procedural events in the encounter transcript.

4. The computer-implemented method of claim 3 wherein processing the encounter transcript to locate the one or more procedural events within the encounter transcript includes one or more of:
    manually initiating the processing of the encounter transcript to locate one or more procedural events within the encounter transcript; and
    automatically initiating the processing of the encounter transcript to locate the one or more procedural events within the encounter transcript.

5. The computer-implemented method of claim 3 wherein processing the encounter transcript to locate the one or more procedural events within the encounter transcript includes:
    associating the one or more procedural events with one or more portions of the encounter information of the patient encounter.

6. The computer-implemented method of claim 1 wherein matching one or more characteristics comprises comparing voice prints for confirming the identity of the one or more encounter participants of the patient encounter.

7. The computer-implemented method of claim 1 wherein the one or more procedural events further includes one or more of:
    a personal medical history event;
    a family medical history event;
    a drug allergy event;
    a drug side-effect event; and
    a drug warning event.

8. A computer program product residing on a non-transitory computer readable medium having a plurality of instructions stored thereon which, when executed by a processor, cause the processor to perform operations comprising:
    obtaining encounter information of a patient encounter, wherein the encounter information includes audio encounter information and machine vision encounter information;
    locating one or more procedural events, wherein at least one of the one or more procedural events includes an informed medical consent event for a medical procedure performed on a patient during the patient encounter;
    confirming an identity of one or more encounter participants of the patient encounter participating in the informed medical consent event using at least one of the audio encounter information and machine vision encounter information, wherein confirming the identity of one or more encounter participants of the patient encounter participating in the informed medical consent event includes at least one of:
        matching one or more voice characteristics of a recording of the audio encounter information to one or more data sources containing matching voice characteristics in a voice print, and
        matching one or more facial characteristics of a recording of the machine vision encounter information to one or more data sources containing matching facial characteristics in a face print; and
    authenticating the informed medical consent event based upon, at least in part, confirming the identity of one or more encounter participants of the patient encounter participating in the informed medical consent event and locating the informed medical consent event for the medical procedure performed on the patient during the patient encounter.

9. The computer program product of claim 8 wherein obtaining encounter information of a patient encounter includes one or more of:
   obtaining encounter information from a medical professional;
   obtaining encounter information from a patient; and
   obtaining encounter information from a third party.

10. The computer program product of claim 8 further comprising:
    processing the audio encounter information of the encounter information to generate an encounter transcript; and
    processing at least a portion of the encounter transcript to populate at least a portion of a medical record associated with the patient encounter; and
    wherein locating the one or more procedural events includes locating the one or more procedural events in the encounter transcript.

11. The computer program product of claim 10 wherein processing the encounter transcript to locate the one or more procedural events within the encounter transcript includes one or more of:
    manually initiating the processing of the encounter transcript to locate one or more procedural events within the encounter transcript; and
    initiating the processing of the encounter transcript to locate one or more procedural events within the encounter transcript.

12. The computer program product of claim 10 wherein processing the encounter transcript to locate the one or more procedural events within the encounter transcript includes:
    associating the one or more procedural events with one or more portions of the encounter information of the patient encounter.

13. The computer program product of claim 8 wherein matching one or more characteristics comprises comparing voice prints for confirming the identity of the one or more encounter participants of the patient encounter.

14. The computer program product of claim 8 wherein the one or more procedural events further includes one or more of:
    a personal medical history event;
    a family medical history event;
    a drug allergy event;
    a drug side-effect event; and
    a drug warning event.

15. A computing system including a processor and memory configured to perform operations comprising:
    obtaining encounter information of a patient encounter, wherein the encounter information includes audio encounter information and machine vision encounter information;
    locating one or more procedural events, wherein at least one of the one or more procedural events includes an informed medical consent event for a medical procedure performed on a patient during the patient encounter;
    confirming an identity of one or more encounter participants of the patient encounter participating in the informed medical consent event using at least one of the audio encounter information and machine vision encounter information, wherein confirming the identity of one or more encounter participants of the patient encounter participating in the informed medical consent event includes at least one of:
       matching one or more voice characteristics of a recording of the audio encounter information to one or more data sources containing matching voice characteristics in a voice print, and
       matching one or more facial characteristics of a recording of the machine vision encounter information to one or more data sources containing matching facial characteristics in a face print; and
    authenticating the informed medical consent event based upon, at least in part, confirming the identity of one or more encounter participants of the patient encounter participating in the informed medical consent event and locating the informed medical consent event for the medical procedure performed on the patient during the patient encounter.

16. The computing system of claim 15 wherein obtaining encounter information of a patient encounter includes one or more of:
    obtaining encounter information from a medical professional;
    obtaining encounter information from a patient; and
    obtaining encounter information from a third party.

17. The computing system of claim 15 further comprising:
    processing the audio encounter information of the encounter information to generate an encounter transcript; and
    processing at least a portion of the encounter transcript to populate at least a portion of a medical record associated with the patient encounter; and
    wherein locating the one or more procedural events includes locating the one or more procedural events in the encounter transcript.

18. The computing system of claim 17 wherein processing the encounter transcript to locate the one or more procedural events within the encounter transcript includes one or more of:
    manually initiating the processing of the encounter transcript to locate one or more procedural events within the encounter transcript; and
    initiating the processing of the encounter transcript to locate one or more procedural events within the encounter transcript.

19. The computing system of claim 17 wherein processing the encounter transcript to locate the one or more procedural events within the encounter transcript includes:
    associating the one or more procedural events with one or more portions of the encounter information of the patient encounter.

20. The computing system of claim 15 wherein the one or more procedural events further includes one or more of:
    a personal medical history event;
    a family medical history event;
    a drug allergy event;
    a drug side-effect event; and
    a drug warning event.

* * * * *